United States Patent [19]

Fuchs et al.

[11] Patent Number: 5,591,604
[45] Date of Patent: Jan. 7, 1997

[54] **RECOMBINANT ANTIBODIES AT THE SURFACE OF *E. COLI***

[75] Inventors: Patrick Fuchs, Heidelberg; Melvyn Little, Neckargemünd-Dilsberg; Frank Breitling; Stefan Dübel, both of Heidelberg, all of Germany

[73] Assignee: Deutsches Krebsforschungszentrum Stiftung des offentlichen Rechts, Heidelberg, Germany

[21] Appl. No.: 982,744
[22] PCT Filed: Jul. 6, 1992
[86] PCT No.: PCT/EP92/01523
§ 371 Date: May 10, 1993
§ 102(e) Date: May 10, 1993
[87] PCT Pub. No.: WO93/01287
PCT Pub. Date: Jan. 21, 1993

[30] Foreign Application Priority Data

Jul. 8, 1991 [DE] Germany ............ 41 22 598.8

[51] Int. Cl.$^6$ .............. C12P 21/08; C12P 21/04; C12N 5/12; C12N 1/20
[52] U.S. Cl. .............. 435/69.7; 435/69.6; 435/320.1; 435/252.3; 435/71.2
[58] Field of Search ............ 435/69.6, 69.7, 435/320.1, 70.23, 252.3

[56] References Cited

PUBLICATIONS

Nature 341, 544–546 (1989).
Science 246, 1275–1281 (1989).
Proc. Natl. Acad. Sci. USA 87, 6450–6454 (1990).
Proc. Natl. Acad. Sci. USA 87, 8095–8099 (1990).
Nature 348, 552–554 (1990).
J. Biochem 86, 991–1000 (1979).
Eur. J. Biochem. 163, 73–77 (1987).
Nature 332, 323–327 (1988).
J. Mol. Biol. 189, 367–370 (1986).
J. Bacteriol. 169, 4379–4383 (1987).
Science 240, 1040–1043 (1988).
J. Biochem. 86, 979–989 (1979).
Science 233, 747–753 (1986).
Proteins: Structure, Function and Genetics, vol. 8, No. 4 1990, Wiley Press, NY, US; pp. 309–314.
Nature 349, 293–299 (1991).
Biotechnology vol. 9, No. 12 (1991), pp. 1369–1372 Fuchs et. al.

*Primary Examiner*—Lila Feisee
*Attorney, Agent, or Firm*—Birch, Stewart, Kolasch & Birch, LLP

[57] ABSTRACT

The present invention relates to a vector expressing a single chain of antibody variable domains coupled to the peptidoglycan associated lipoprotein (PAL) of *E. coli*. Furthermore, the present invention relates to the use of this vector and to a method for the isolation of cells producing specific antibodies.

6 Claims, 2 Drawing Sheets

Fig. 1a

[Plasmid map: pAP1 with Amp^r, LEADER, V_H, V_L, PAL regions; restriction sites PstI, TAG-LINKER, BamHI, EcoRI; P/O;RBS, T1, T2]

Fig. 1b

```
         RBS
GAATTCATTAAAGAGGAGAAATTAACTTCATGAAATACCTCTTGCTGCTCTGGCTGCTTGCTGCTGGCTGGCTGCTGGCAGCT
EcoRI                       MetLysTyrLeuLeuProThrAlaAlaAlaGlyLeuLeuLeuLeuAlaAla
                                                                        (NcoI)
-5                     -1  VH                                                    tag-Linker
CAGCCCGGCGGATGGGCGAAGTTCAGCTGCAG...TCAGGGAGTGCATCCGCCCCAAAGCTTGAAGAAGGTGAATTCTCAGAA
GlnProAlaMetAlaGlnValGlnLeuGln...SerGlySerAlaSerAlaProLysLeuGluGluGlyGluPheSerGlu
                             PstI                             HindIII        EcoRI pelB leader       -6

1  VL                                                113          2  PAL                12
GCGCGCGAAGATATC...TAGAAACGTACGGTAGCAGCTCCTGGATCCTCCAACAAGAACGCCAGCAATGACGGCCAGCGAA
AlaArgGluAspIle...IleLysArgThrValAlaAlaAlaProGlySerSerAsnLysAsnAlaSerAsnAspGlySerGlu
BssHI  EcoRV                                         BamHI

LysAsnArgArgAlaValLeuValValTyrStop
AAAAACCGTCGTGCGGTACTGGTTACTAAGAGAATTCCATGATC..........
                              EcoRI  (BclI)
               forward  Primer  GCGGCAGGATCCTCCAACAAGAACGCCAGC
                            CCAAATGATTCTCTTAAGGTACTAGTCATTGAAG
                            backward  Primer
```

RECOMBINANT ANTIBODIES AT THE SURFACE OF E. COLI

The invention concerns vectors that express single chain antibodies coupled to the surface of antibody-producing cells. Furthermore, the invention embraces the use of these vectors to rapidly isolate single cells producing specific antibodies. Finally, the invention provides a method for the isolation of cells producing specific antibodies.

Previous screening procedures for recombinant antibodies have employed ELISA assays of bacterial supernatants (Nature 341, 544–546 (1989)) or radioactively labeled immunogens for screening nitrocellulose plaque lift-offs of bacterial colonies infected with phage expression vectors (Science 246, 1275–1281 (1989); Proc. Natl. Acad. Sci. USA 87, 6450–6454 (1990); Proc. Natl. Acad. Sci. USA 87 8095–8099 (1990)). However, for the selection of specific antibodies from randomly combined light and heavy chain libraries that do not contain a preponderance of antibodies to a particular antigen, the task of screening millions of antibody clones would be greatly facilitated by targeting antibodies to the surface of bacteria or viruses. Immobilized antigens could then be used to select specific antibodies.

A viral system for the surface presentation of antibodies has recently been disclosed in Nature, 348, 552–554 (1990). Single chain variable domains (the precursors of applicant's own antibody construct) were fused to the docking protein (protein p III) of phage particles. Phages bearing the fusion protein were able to be enriched on columns of antigen.

However, these fusion phages have been shown to be mainly useful for displaying relatively small inserts, probably because the larger inserts have an adverse effect on the infectivity function of p III. Libraries of "phage antibodies", therefore, run the risk of being quickly dominated by deletion mutants. Furthermore, relatively large numbers of phage particles appear to bind unspecifically to columns of immobilized antigen.

Thus the technical problem underlying this invention is to provide a more efficient mean for screening antibody libraries in bacteria.

This problem is solved by providing a vector that expresses single chain antibody variable domains coupled to the peptidoglycan associated lipoprotein of E. coli (PAL, J. Biochem. 86, 991–1000 (1979); Eur. J. Biochem., 163, 73–77 (1987)).

PAL is a cell envelope component of E. coli that is particularly resistant to solubilization by SDS (J. Biochem. 86, 991–1000 (1979)). Its peptidoglycan associated protein component has a molecular mass of 16600 (Eur. J. Biochem., 163, 73–77 (1987)) and is modified at the amino-terminal cysteine by a lipid moiety that is integrated into the outer membrane. The attachment of antibodies to the amino-terminus of PAL therefore is a means of presenting them for antigen binding at the cell surface.

The antibody-PAL fusion protein was identified on the cell surface by a monoclonal antibody to an epitope in the linker sequence between the heavy and light chains. It was able to bind antigen and was tightly bound to the murein layer of the cell envelope. Immunofluorescence studies on unfixed cells showed that functional antibody domains were quite accessible at the cell surface.

A major attraction of the bacterial system of this invention is that an abundance of antibody molecules are available for binding in contrast to the five antibody fusion molecules that are bound per particle in the phage system. The use of immunofluorescently labeled antigens should therefore provide a rapid means of isolating cells producing specific antibodies. Screening with a fluorescence assisted cell sorter (FACS), for example, could theoretically provide an enrichment of at least $10^6$ in one step since more than several million bacteria can be scanned at one time and single bacteria can be selected. Alternatively, bacteria expressing specific antibodies could be selected by binding to immobilized antigens. Further advantages include the efficiency of transformation, the ease of propagation and the absence of selection pressure to remove antibody DNA during library amplification.

A preferred use of the instant invention is to rapidly isolate antibodies to tumor-associated antigens by differential screening analyses. For example, after first depleting a library of antibodies to the cell surface antigens of normal tissue, the cells of neoplastic tissue should only bind those antibodies specific to any differences. This procedure could also be used for detecting antigenic differences between any closely related cells or organelles. The PAL vector system described in this investigation could prove to be equally useful for presenting other proteins and peptides at the surface of E. coli. This might then facilitate the production of live vaccines. For example, epitopes inserted within cell surface loops of the outer membrane LamB protein of gram negative bacteria have been used to generate antibodies. For these purposes, the apparent lack of effect on bacterial growth of the overexpressed PAL fusion protein might prove to be particularly advantageous.

BRIEF DESCRIPTION OF THE DRAWINGS

FIG. 1(a) is a restriction map of the antibody -PAL expression plasmid pAP1.

FIG. 1(b) discloses the ribosome binding site (RBS), leader sequence of pectate lyase, Tag-linker, the peptidoglycan associated protein (PAL) sequence and the PCR primers.

DETAILED DESCRIPTION OF THE INVENTION

Figure 2A:
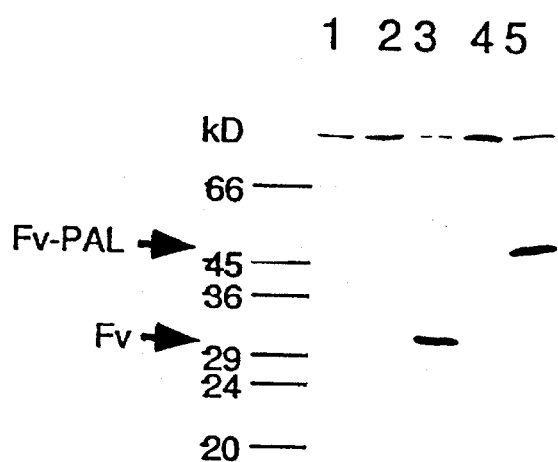
FIG. 2(a) shows the results of Western blot analysis of the antibody -PAL fusion protein.

The following Examples illustrate but not restrict the present invention.

EXAMPLE 1

To synthesize an antibody-PAL fusion protein, DNA coding for the heavy and light chain variable domains of a humanized antibody against chick lysozyme (disclosed in Nature 332, 323–327 (1988)) linked by eighteen amino acids containing the epitope of the tubulin monoclonal antibody YOL1/34 (J. Mol. Biol. 189, 367–370 (1986)) was used. Besides providing a means of identification, the linker sequence was added to facilitate dimerization of the two chains and to hinder their disassociation.

A flexible junction to PAL was provided by extending the light chain to include the first six amino acids of the constant domain. To facilitate transport across the cytoplasmic membrane, DNA coding for the leader sequence of the enzyme pectate lyase was ligated to the 5' end of the heavy chain DNA (Lei et al, 1987; Better et al., 1988) and PAL-DNA, amplified from the plasmid pRC2 (Chen and Henning, 1987), was then joined to the antibody DNA (FIG. 1) (SEQ ID NOS: 1 to 3). One small difference between the natural and in vitro synthesized PAL was the exchange of the amino-terminal cysteine that normally carries the lipid moiety for glycine.

The pAP1 plasmid has been deposited under the terms of the Budapest Treaty with American Type Tissue Culture Collection (ATCC), 12301 Parklawn Drive, Rockville, Md. 20852, USA and can be obtained under the ATCC designation No. 97104.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 110 base pairs
        ( B ) TYPE: nucleic acid
        ( C ) STRANDEDNESS: double stranded
        ( D ) TOPOLOGY: linear ( i x ) FEATURE:
        ( A ) NAME/KEY: CDS
        ( B ) LOCATION: 30 .. 110

( i x ) FEATURE:
        ( A ) NAME/KEY: RBS
        ( B ) LOCATION: 11 .. 17

( x i ) SEQUENCE DESCRIPTION: SEQ ID NO: 1:

```
GAATTCATTA AAGAGGAGAA ATTAACTCC ATG AAA TAC CTC TTG CCT ACG GCA      53
                                Met Lys Tyr Leu Leu Pro Thr Ala
                                 1               5

GCC GCT GGC TTG CTG CTG CTG GCA GCT CAG CCG GCG ATG GCG CAA GTT     101
Ala Ala Gly Leu Leu Leu Leu Ala Ala Gln Pro Ala Met Ala Gln Val
         10              15                  20

CAG CTG CAG                                                         110
Gln Leu Gln
 25
```

( 2 ) INFORMATION FOR SEQ ID NO:2:

( i ) SEQUENCE CHARACTERISTICS:
        ( A ) LENGTH: 63 base pairs
        ( B ) TYPE: nucleic acid
        ( C ) STRANDEDNESS: double stranded
        ( D ) TOPOLOGY: linear ( i x ) FEATURE:
        ( A ) NAME/KEY: CDS
        ( B ) LOCATION: 1 .. 63

( i x ) FEATURE:
        ( A ) NAME/KEY: CDS
        ( B ) LOCATION: 2 .. 63
        ( D ) OTHER INFORMATION: /product ="protein containing the
            epitope for the tubulin monoclonal antibody YOL1/34

( x i ) SEQUENCE DESCRIPTION: SEQ ID NO: 2:

```
TCA GGG AGT GCA TCC GCC CCA AAG CTT GAA GAA GGT GAA TTC TCA GAA      48
Ser Gly Ser Ala Ser Ala Pro Lys Leu Glu Glu Gly Glu Phe Ser Glu
 1               5                  10                  15

GCG CGC GAA GAT ATC                                                  63
Ala Arg Glu Asp Ile
             20
```

( 2 ) INFORMATION FOR SEQ ID NO:3:

( i ) SEQUENCE CHARACTERISTICS:
        ( A ) LENGTH: 108 base pairs (B) TYPE: nucleic acid
(C) STRANDEDNESS: double stranded
(D) TOPOLOGY: linear (ix) FEATURE:
(A) NAME/KEY: CDS
(B) LOCATION: 1 .. 90

(xi) SEQUENCE DESCRIPTION: SEQ ID NO: 3:

| TAG | AAA | CGT | ACG | GTA | GCA | GCT | CCT | GGA | TCC | TCC | AAC | AAG | AAC | GCC | AGC | 48 |
| Ile | Lys | Arg | Thr | Val | Ala | Ala | Pro | Gly | Ser | Ser | Asn | Lys | Asn | Ala | Ser | |
| 1 | | | | 5 | | | | | 10 | | | | | 15 | | |

| AAT | GAC | GGC | AGC | GAA | AAA | AAC | CGT | CGT | GCG | GTA | CTG | GTT | TAC | 90 |
| Asn | Asp | Gly | Ser | Glu | Lys | Asn | Arg | Arg | Ala | Val | Leu | Val | Tyr | |
| | | | 20 | | | | | 25 | | | | | 30 | |

TAAGAGAATT CCATGATC                                                                        108

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(B) LOCATION: 1 .. 30
(D) OTHER INFORMATION: primer (xi) SEQUENCE DESCRIPTION: SEQ ID NO: 4:

GCGGCAGGAT CCTCCAACAA GAACGCCAGC                                                            30

(2) INFORMATION FOR SEQ ID NO:5:

(i) SEQUENCE CHARACTERISTICS:
(A) LENGTH: 34 base pairs
(B) TYPE: nucleic acid
(C) STRANDEDNESS: single
(D) TOPOLOGY: linear (ix) FEATURE:
(B) LOCATION: 1 .. 34
(D) OTHER INFORMATION: primer (xi) SEQUENCE DESCRIPTION: SEQ ID NO: 5:

CCAAATGATT CTCTTAAGGT ACTAGTCATT GAAG                                                       34

(2) INFORMATION FOR SEQ ID NO:6:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 6:

| Gly | Ser | Ala | Ser | Ala | Pro | Lys | Leu | Glu | Glu | Gly | Glu | Phe | Ser | Glu | Ala |
| 1 | | | | 5 | | | | | 10 | | | | | 15 | |

Arg Glu

EXAMPLE 2

Figure 2B:
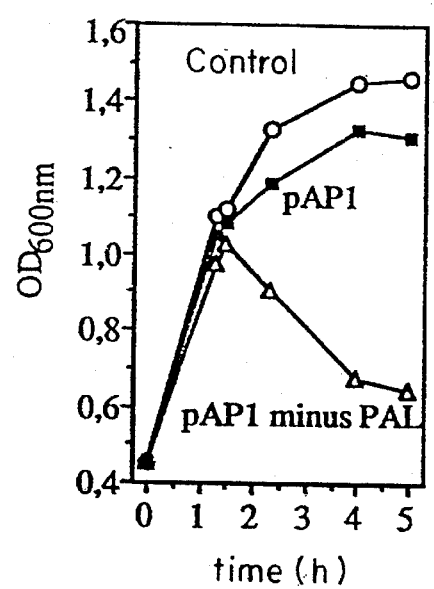
FIG. 2(b) plots the growth curve of E. coli transformed with pAP1, pAP1 minus PAL DNA and pAP1 minus antibody -PAL DNA.

To test whether the full length fusion protein could be expressed, 1 mM IPTG was added to a log phase culture of E. coli transformed with pAP1. On western blots of SDS polyacrylamide gels, the antibody-PAL fusion protein was identified by a monoclonal antibody to the marker peptide in the linker sequence between the heavy and light chains (FIG. 2a). Its apparent molecular weight of about 48 kd was somewhat higher than the predicted Mr 45000, probably due to the aberrant electrophoretic mobility of PAL. The presence of a minor band of lower molecular weight indicated a small degree of proteolysis. A higher molecular weight cytoplasmic component of E. coli that cross-reacted with YOL1/34 was present in all cells. Comparisons of the growth rates of E. coli transformed with pAP1 and pAP1 minus antibody-PAL DNA after addition of IPTG showed little difference over a period of five hours. In contrast, an identical culture of E. coli transformed with pAP1 minus PAL DNA, which only expressed single chain antibody started to lyse after two hours (FIG. 2b).

EXAMPLE 3

To investigate the binding of the fusion protein to the cell wall, bacteria were ruptured by shaking with glass beads in a cell disintegrator and extracted with 1% SDS at 10° C. The residual material was incubated with 1% SDS for 1 h at 30° C. and then with 1% SDS for 1 h at 50° C. A western blot analysis and stained polyacrylamide gels showed that although some of the fusion protein was removed at 30° C., the major part required higher temperatures in order to be released. These binding characteristics are extremely similar to those described for PAL alone (J. Biochem. 86, 991–1000 (1979); J. Biochem. 86, 979–989 (1979)) and enabled highly enriched samples to be prepared in a few simple steps. Native PAL protein migrates with an apparent molecular weight of around 20 kd and probably corresponds to a protein of this molecular weight that co-purified with the fusion protein. A densitometric comparison of the amounts of fusion protein and the putative PAL protein indicated that about five times more fusion protein was present than native PAL.

Surprisingly, a small portion of the fusion protein was released into the medium, even near the beginning of the logarithmic phase where no signs of cell lysis could be detected. This might possibly be due to saturation of PAL binding sites and a facilitated transport or leak of antibody domains through the outer membrane. To determine whether the fusion protein could bind antigen, the medium was passed over a column of lysozyme coupled to sepharose. Gel electrophoresis and western blotting of the unbound material and the fractions obtained after extensive washing and elution with 0.05M diethylamine showed that the fusion protein was indeed specifically retained on the lysozyme column.

EXAMPLE 4

The accessibility of the bound antibody to extracellular proteins at the surface of unfixed cells was tested by incubating E. coli with the monoclonal antibody YOL1/34 and then with a fluorescently labeled anti rat serum. E. coli expressing the antibody-PAL fusion protein showed a strong fluorescence that was especially intense at the periphery and at the junctions within short chains. In contrast, E. coli that did not express the fusion protein were not fluorescent. Experiments with fixed cells gave the same results. This clear accessibility at the cell surface may not only result from targeting to the outer membrane by PAL and the propensity of antibody domains to cross it but also from the effect of PAL on outer membrane structure. Measurements of β-lactamase, a soluble periplasmatic protein, showed that much more was present in the medium of cells expressing the fusion protein than in the medium of cells not expressing the fusion protein.

Incubations of unfixed cells with the biotinylated antigen, chick lysozyme, while somewhat harmful to cellular integrity, demonstrated the ability of the fusion protein to bind antigen in situ. After extensive washing and incubation with fluorescent avidin, E. coli-pAP1 showed a marked fluorescence. E. coli transformed with pAP1 minus antibody-PAL DNA showed no fluorescence.

Accessibility of functional antibody domains at the cell surface: E. coli transformed with pAP1 minus antibody-PAL DNA and with pAP1 were incubated with YOL1/34 and a fluorescein labeled second antibody or with biotinylated lysozyme and fluorescein labeled avidin.

Method:

Cells were washed in PBS and allowed to settle onto poly-L-lysine coated glass slides for 20 min at 4° C. They were then incubated for 1 h at 37° C. with the monoclonal antibody YOL1/34 diluted 1:100 in PBS. After washing in PBS, they were incubated for 1 h at 37° C. with anti rat IgG-FITC diluted 1:100 and washed again in PBS. For antigen binding, chick lysozyme was biotinylated, diluted 1:20 in PBS and incubated with the cells for 1 h at 37° C. After extensive washing with PBS, the cells were incubated for 1 h at 37° C. with FITC-avidin diluted 1:1000 and washed again in PBS.

It should also be possible to attach other proteins and peptides to the cell wall provided that they can be secreted when fused to a bacterial leader sequence. This might then facilitate the production of live vaccines. For these purposes, the apparent lack of effect on bacterial growth of the overexpressed PAL fusion protein might prove to be particularly advantageous.

Legends to the Figures

FIG. 1 (SEQ ID NOS: 1 to 5) Antibody-PAL expression plasmid pAP1 P/O: promoter/operator; RBS: ribosome binding site; Leader: signal sequence of pectate lyase; Tag-Linker: eighteen amino acids containing the epitope for the tubulin monoclonal antibody YOL1/34; PAL: peptidoglycan associated protein. Construction: DNA coding for the heavy and light variable domains of a humanized chick lysozyme antibody derived from the monoclonal antibody D 1.3 (Amit et al., Science 233, 747–754 (1986)) was linked by DNA coding for eighteen amino acids (GSASAPKLEE-GEFSEARE) SEQ ID NO: 6 that included the epitope for YOL1/34. The light chain DNA was extended to include nucleotides coding for the first six amino acids of the constant domain. This was then ligated to the 3' end of DNA coding for the signal sequence of the enzyme pectate lyase that had been inserted into the Nco 1 site of the slightly modified expression plasmid pKK233-2 (Clontech, Palo Alto, Calif., USA). PAL DNA that had been amplified from the plasmid pRC2 using primers shown in FIG. 1 (SEQ ID NOS: 4 and 5) was then joined to the antibody DNA. The sequence of the inserted PAL was identical to native PAL except that the aminoterminal cysteine had been exchanged for glycine.

FIG. 2 Expression and binding properties of the antibody-PAL fusion protein (a) Western blots of induced fusion protein after addition of 1 mM IPTG. 1, pAP1 minus antibody-PAL DNA (+IPTG); 2, pAP1 minus PAL DNA (−IPTG): 3, pAP1 minus PAL DNA (+IPTG); 4, pAP1 (−IPTG); 5, pAP1 (+IPTG).

(b) Growth curve of *E. coli* transformed with pAP1, pAP1 minus PAL DNA and pAP1 minus antibody-PAL DNA (control) after induction with 1 mM IPTG.

Induction and extraction of antibody-PAL:

*E. coli* strain BMH71/18 carrying pDMI that expresses lac repressor were-transformed with pAP1 and pAP1 precursors. Cells in 125 ml of LB medium were grown to OD 0.45 at 600 nm, induced with 1 mM IPTG and harvested after 1.5 h. For SDS extractions, the cells were suspended in 3 ml $H_2O$ and ruptured by shaking in a cell disintegrator for 5 min with 5 ml of glass beads (diameter 0.13 mm) and 0.5 mg DNase 1. After adjusting to 1% SDS in 10 mM Tris, pH 7.5, the cell lysate was sedimented at 42000 g for 45 min at 10° C. The pellet was resuspended in 1% SDS/10mM Tris/10 % glycerine, pH 7.8 for 1 h at 30° C. and sedimented-as before. This step was repeated at 50° C. Fusion proteins were detected on western blots with the monoclonal antibody YOL1/34. Prior to antibody staining the blots were stained for proteins with Ponceau S. Polyacrylamide gels were stained with Coomassie blue. For affinity chromatography, chick lysozyme was coupled to cyanogen bromide activated Sepharose according to the instructions of the manufacturer. The lysozyme-Sepharose was incubated for 20 min at room temperature with 10 ml of medium and poured into columns that were subsequently washed two times with ten bed volumes of PBS before eluting with 0.05M diethylamine.

We claim:

1. A vector which comprises the DNA sequence coding for a single chain of antibody variable domains coupled to the DNA sequence coding for the peptidoglycan associated lipoprotein (PAL) of *E. coli*.

2. The vector according to claim 1, wherein said vector is the plasmid pAP1 described in FIG. 1*a*.

3. A method for the isolation of cells producing specific antibodies, which comprises (a) transforming bacteria with a vector according to claim 1 or 2, (b) selecting bacteria expressing specific antibodies on the cell surface by fluorescence assisted cell sorting (FACS) or by binding to immobilized antigens and (c) isolating said bacteria selected in (b).

4. A method for expressing a peptide or protein on the surface of bacteria comprising transforming said bacteria with a vector, said vector comprising a DNA sequence encoding said peptide or protein fused to a DNA sequence encoding the peptidoglycan associated lipoprotein, PAL, of *E. coli*.

5. A vector which comprises a DNA sequence encoding a peptide or protein coupled to the DNA sequence coding for the peptidoglycan associated lipoprotein (PAL) of *E. coli*.

6. A method of expressing an antibody Fv on the surface of bacteria comprising transforming said bacteria with a vector according to claim 1 or 2.

* * * * *